United States Patent [19]

Anderson et al.

[11] Patent Number: 5,176,622
[45] Date of Patent: Jan. 5, 1993

[54] STOOP LABOR ASSIST DEVICE

[75] Inventors: Robert B. Anderson; Richard M. Deamer, both of Ventura, Calif.

[73] Assignee: BNDR Associates, Ventura, Calif.

[21] Appl. No.: 771,443

[22] Filed: Oct. 4, 1991

[51] Int. Cl.⁵ .............................................. A61F 5/00
[52] U.S. Cl. ........................................ 602/19; 602/16; 482/124; 482/127; 482/131
[58] Field of Search .................. 602/5, 16, 19; 2/44, 2/45; 482/105, 131, 121, 122, 124, 125, 127; 16/286; 267/30, 152; 623/53, 58

[56] References Cited

U.S. PATENT DOCUMENTS

| | | | |
|---|---|---|---|
| 3,814,419 | 6/1974 | Bjorklund et al. | 482/124 |
| 4,483,533 | 11/1984 | Mangiapane | 482/139 X |
| 4,623,141 | 11/1986 | Salvino | 482/127 X |
| 4,681,315 | 7/1987 | Yang | 482/127 X |
| 4,753,434 | 6/1988 | Salvino | 482/121 X |
| 4,817,921 | 4/1989 | Stevenson | 267/152 X |
| 4,829,989 | 5/1989 | Deamer et al. | 128/78 |
| 4,905,678 | 3/1990 | Cumins et al. | |
| 5,042,804 | 8/1991 | Uke et al. | 273/81 R X |
| 5,054,476 | 10/1991 | Petrofsky et al. | |

Primary Examiner—Richard J. Apley
Assistant Examiner—Linda C. M. Dvorak
Attorney, Agent, or Firm—Marvin E. Jacobs

[57] ABSTRACT

A hip mounted, springable frame that compresses between the chest and thighs of a worker when he stoops over so as to help the worker to stand erect again and ease back strain. The center of the frame comprises a pair of arc-shape springs that wrap around cylindrical spools of elastomer. The spools are attached to a belt surrounding the worker's waist at hip level. The frame is easily removed and reattached by snapping the springs over the spools. Wear is reduced since there are no moving parts, and the spring forces are adjustable with the use of variable compliance and or springs having different spring constant such as priorities by different spring geometry.

15 Claims, 2 Drawing Sheets

STOOP LABOR ASSIST DEVICE

TECHNICAL FIELD

This invention relates to devices to reduce stress on back muscles caused by repeated bending over during stoop labor activities; particularly, spring loaded, body conforming frames that compress when the user bends down, and expand again upon the user standing up, to help the back muscles raise the user's body to a standing position.

BACKGROUND OF THE INVENTION

Any task requiring a lot of bending, such as yard or field work, is very tiring and even potentially damaging to the muscles and joints of the back. A good way to reduce this stress is disclosed in U.S. Pat. No. 4,829,989, issued to Deamer et al. The Deamer patent teaches a light weight frame, hinged and sprung at the waist, so as to be compressed between the chest area of the upper torso and the front thigh area of the legs, just above the knees, when the user bends over. As the user again stands up, the springs of the frame, braced against the thighs, expand the frame so as to push upward on the chest and greatly lessen the forces that the back muscles need generate. The device stores energy upon compression and returns it to the system upon body erection. This energy is roughly equivalent to the energy required by the back muscles to perform the same function and is hence replaced by the device. Advantages of this frame design include a hinge axis aligned with the natural pivot axis of the body to better move with the body, and torsionally adjustable springs to better match the force requirements of different bodies. The complete teachings of the Deamer U.S. Pat. No. 4,829,989 are incorporated herein by reference, since they are fully relevant to the improvements herein described.

SUMMARY OF THE INVENTION

Briefly, this invention contemplates a substantial improvement to the above described springable body frame. A new hinge design is presented that comprises an arcuate shaped spring that wraps snugly about a cylindrical spool of flexible and compressible elastomer. Any natural or synthetic elastomer, such as polyurethane, can be utilized. The elastomer can be a foam. The spool is, in turn, mounted on a hip belt about the user's waist, to locate the spool slightly below the iliac crest. Since the arcuate spring is integral with the frame that contacts the thighs and chest, the entire frame may be easily removed from the body as a unit simply by unsnapping the spring from the spool that supports it. This allows the user to walk about without the frame, if desired, but quickly and easily put the frame back on when stoop labor is resumed.

The new hinge design has the additional benefit of being a one-piece hinge with no moving parts. Pivoting or sliding parts, that are movable relative to each other, may wear more easily, especially in the dirty environment associated with stoop labor.

The spring force may be adjusted to match different weight users by use of elastomers having a selected elasticity. This elasticity can be adjusted by use of foams having different densities. As the arcuate spring bends, it compresses the spool within the arc of the spring. Hence, part of the spring force is contributed by the spool itself. Changing the spool compressibility, therefore, alters the restoring force of the body frame.

In summary, then, the improved hinge design accomplishes the original goals of adjustability and being located at the waist, in line with the natural body bending axis, and also allows a simpler, lower-cost, lighter-weight frame with no moving parts, that can be readily detached and reattached as desired. Further benefits and details are elucidated in the drawings and the detailed description thereof that follows.

DETAILED DESCRIPTION OF THE INVENTION

Figures 1, 2, 3:
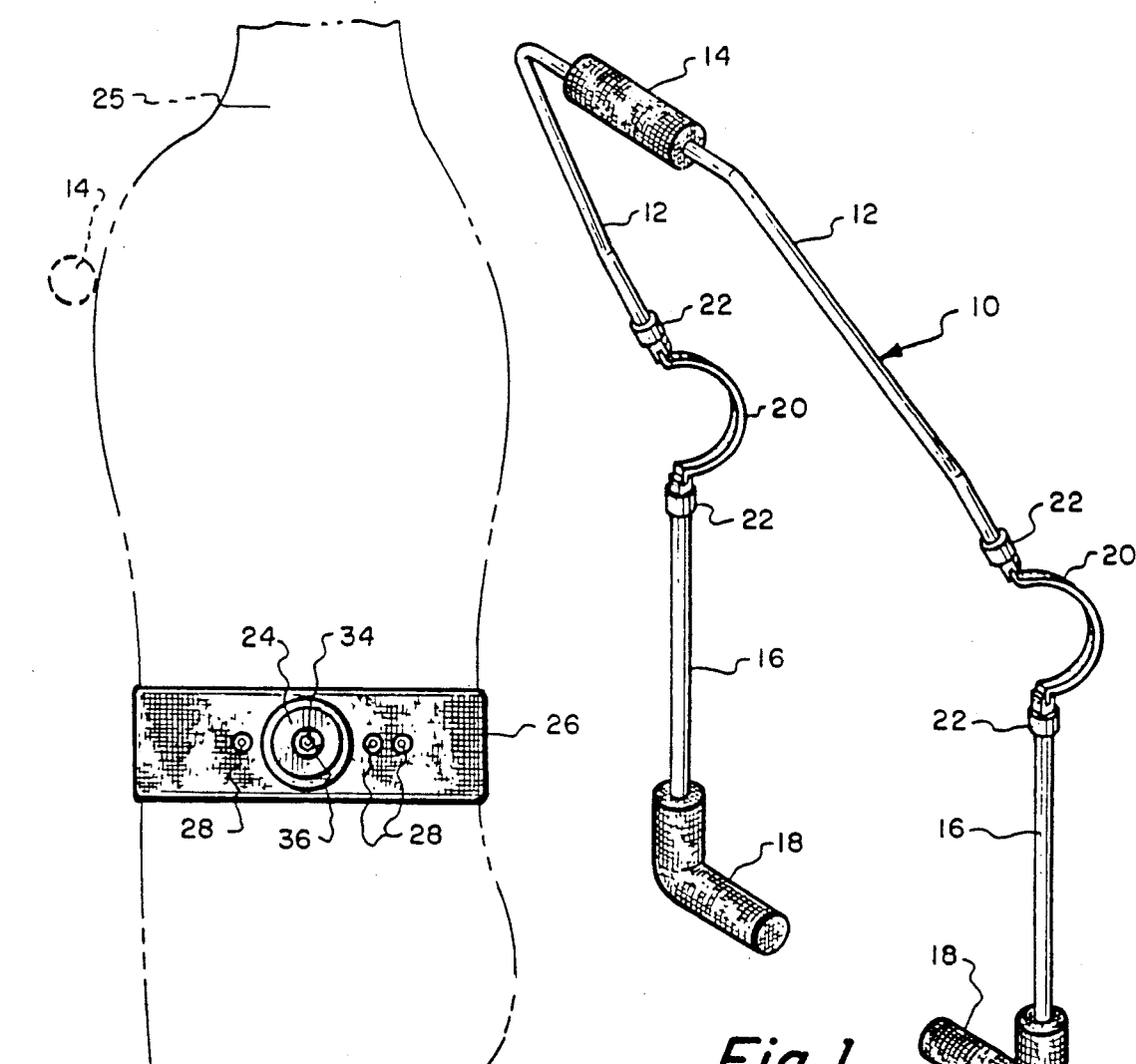
FIG. 1 shows the integral, one piece, compressible frame of the present invention, in perspective, with the novel arcuate springs forming a central portion thereof.
FIG. 2 is a partial representational view of a worker's body, with the support belt of the present invention worn about the body, showing one of the compressible spools around which the arcuate spring snaps to secure the frame to the body.
FIG. 3 shows the frame snapped on the belt mounted elastomer spools, with the worker bending over so as to compress the frame between the thighs and the chest.

The detached one-piece frame 10 of the present invention is shown in FIG. 1. An upper torso-engaging portion 12 has a padded chest contacting region 14 that could comprise, for example, a cylinder of fabric-wrapped foam positioned about the frame members 12. Frame 10 has a pair of lower, thigh engaging, L-shaped tubes 16, also wrapped with suitable pads 18. The upper and lower tubes are solidly connected to each other by a pair of arcuate springs 20 that fasten to the frame 10 with four connectors 22, described with respect to FIG. 5.

The torsio-leaf spring 20 provides the major spring restoring force mechanism. The compliant spool 24 provides an adjustment means for accommodating increased body weight of potential wearers. For extremely massive individuals, a larger sized unit with stronger steel springs could be fitted. The illustrated embodiment employs a torsio-leaf spring design suitable for the median-sized male wearer of approximately 155 lbs., with minimal assistance from the spool. Thus, an increased spring constant of, say, approximately 25-30% could be provided by installing a less compliant spool. Tests show that stiffer than necessary spring rates are acceptable to a point, and are preferred over slightly softer than necessary spring rates. Thus, lighter-weight wearers will most likely respond favorably to the median sized/sprung unit, even though it is stiffer than the theoretical ideal. These units would employ the most compliant spool.

Springs 20 have a diameter chosen to fit tightly about the circumference of flexible and compliant elastomer spools 24, one of which is visible in FIG. 2. A body outline 25 is diagrammed in FIG. 2 to show how a suitable belt 26 fits around a worker's waist, positioned on his hips. Belt 26, alone, does not encumber the worker at all. Several holes 28 are provided in belt 26 to ensure that the spool 24 can be mounted at a location in alignment with the normal flexion center of rotation of the body. Spool 24 is mounted in the correct hole 28 for the worker's body size. When the worker is ready to begin assisted stoop labor, he can quickly and easily snap the arcuate springs 20 around the spools 24 on each side of his body. When the frame is in place, the normal position of pad 14 is against the chest, as shown in FIG. 2 by dashed line 14, and the thigh pads 18 are displaced in front of the thighs, as shown by dashed line 18. Thus, in the standing position, the worker may easily walk about without bumping his legs into pads 18.

FIG. 3 shows how the frame 10 is compressed when the worker bends forward. Thigh pads 18 rest against the thighs. Pad 14 is pushed forward and down by the chest. Springs 20 flex themselves, and also compress spools 24 so as to store energy in the system and to develop a restoring force against the chest that helps the worker to stand up again.

Figure 4:
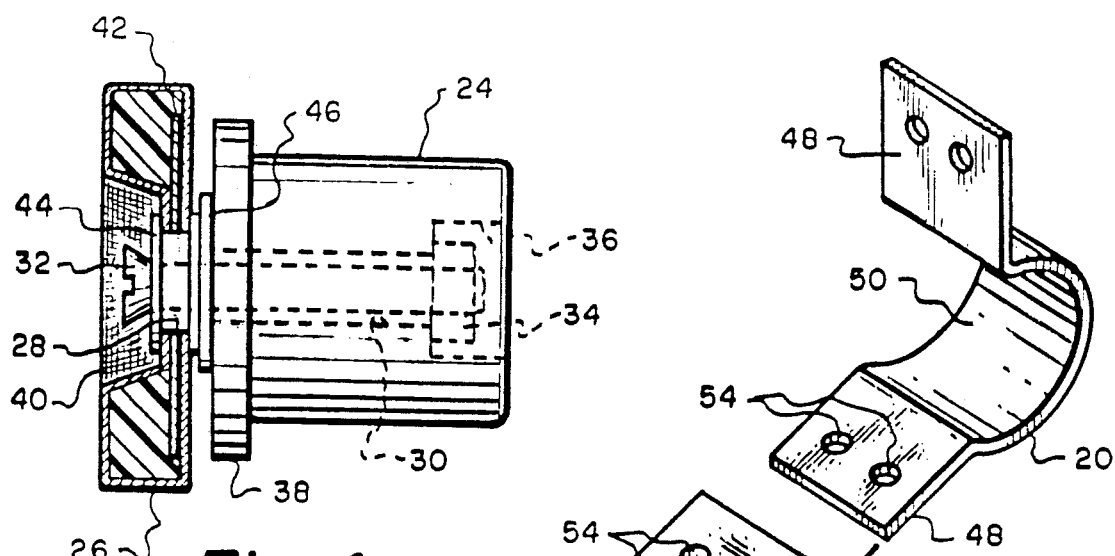
FIG. 4 is an elevational view of one of the spools, revealing how the spool is supported on the belt.

Spools 24 are shown in greater detail in FIG. 4. Spool 24 includes a tubular hub 30, of aluminum or the like, through which a suitable mounting screw 32 is secured with a nut 34. A recess 36 may be provided in the end of spool 24 to contain nut 34 and avoid contact with the worker's arm. A raised shoulder 38 helps keep the spring 20 from chafing against belt 26. Belt 26 may comprise a foam-filled nylon fabric, for a comfortable fit, with relieved areas 40 for the screws 32. Belt 26 also includes a flat reinforcing member 42 within, in the area of the holes 28, to make the belt stiffer and keep the screws 32 perpendicular to the belt. Each screw 32 extends through a grommet 44 mounted in the holes 28. The assembly may include an anti-friction washer 46.

Figure 5:
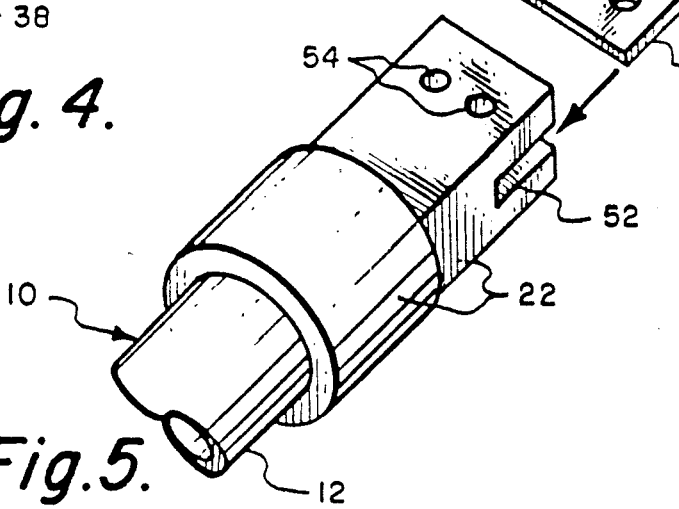
FIG. 5 is a perspective view of the arcuate spring that wraps around the spools, along with an exemplary connector to make the arcuate spring integral with the tube members that form the frame.

FIG. 5 shows one of the springs 20 in greater detail. The arcuate portion 50 is sized to fit snugly about the circumference of spool 24, while the end tabs 48 fit into slots 52 in connectors 22. Holes 54 allow connectors 22 to be bolted to tabs 48. Arcuate portion 50 extends more than halfway around spool 24 so as to grip spool 24, even when the spring is relaxed. In the preferred embodiment, arcuate spring 20 wraps around about five-eighths of the circumference of spool 24, but this figure may vary.

Spool 24 is constructed of any springable and compressible material, such as a bulk or foamed elastomer. Foam materials of durometer Shore 25A to 55A have been found to work well with two-inch diameter spools; also, this is not the limit of usable materials. When spring 20 flexes inward against spools 24, the spools are effectively pinched between the ends of arcuate portions 50 and the frame 10 cannot accidently come off and cause injury to the worker. Thus, the frame, though easily attached and removed from the worker's belt at rest, is firmly locked in place during use. This pinching action, however, causes a certain limit on the compression of the frame. For greater deflections, or for different spring rates, the alternate embodiments of FIGS. 6 and 7 may be employed.

Figure 6:
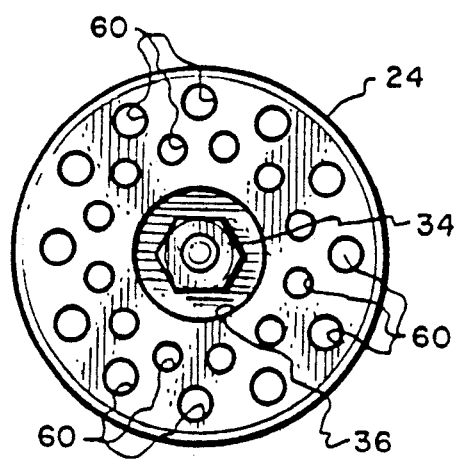
FIGS. 6 and 7 are right-hand end views of a spool, as viewed in FIG. 4, showing spools that are modified in shape to achieve variations in compressibility, and consequently variations in the spring restoring forces of the frame.
Figure 7:
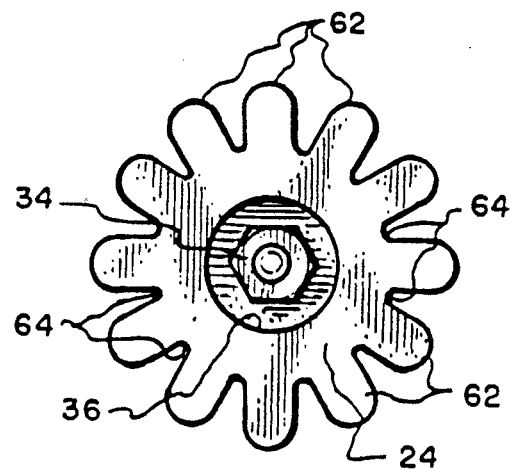

FIG. 6 shows how a number of voids 60 may be molded into the body of spool 24 to allow it to more easily squeeze to a smaller diameter inside spring 24. FIG. 7 shows a different possibility with spool 24 molded to have a series of flutes 62 with voids or indentations 64 therebetween, also easier to squeeze down to a smaller size. Clearly, many other variations are also possible within the spirit and scope of the invention, and therefore limitation is intended only in accordance with the following claims.

We claim:
1. A device to assist an individual to stand up again, after bending at the waist, so as to reduce stress and strain on the back of the individual comprising:
    belt means adapted to grasp the hip area of the individual;
    compressible spool means mounted on said belt means;
    a detachable and integral frame having a chest-engaging upper portion and a thigh-engaging lower portion; and
    arcuate spring means attached between said upper and lower portions so as to allow the portions to springably flex relative to each other, said spring means sized and shaped to fit closely on and about said spool means, and said arcuate spring means extending more than half way around said spool means, but not all the way around said spool means, so that said integral frame can be quickly and easily detached from said compressible spool means, as a unit, by compressing said spool means and flexing the arcuate spring means wider.

2. The device of claim 1 in which said spool means comprises a pair of spools, mounted one on each side of the individual, generally in alignment with the natural bending axis of the body.

3. The device of claim 2 in which said spools comprise an elastomer.

4. The device of claim 3 in which said elastomer has a durometer in the range of Shore 25A to 55A.

5. The device of claim 3 in which said spools are molded with voids or flutes therein to vary compliance and final compressed shape.

6. The device of claim 1 in which the arcuate spring means is generally cylindrical in the central part thereof, and said spool means is also generally cylindrical and of about the same diameter as the inside surface of the arcuate spring central part.

7. The device of claim 6 in which the arcuate spring means is comprised of generally thin strip material having a variable width and thickness adapted to vary spring constant, depending on the request of the user.

8. The device of claim 6 in which said arcuate spring central part extends about five-eighths of the way around said spool means.

9. The device of claim 8 in which said spool means comprises a pair of spools, mounted one on each side of the individual, generally in alignment with the natural bending axis of the body.

10. The device of claim 8 in which said spools comprise an elastomer.

11. The device of claim 10 in which said elastomer has a durometer in the range of Shore 25A to 55A.

12. The device of claim 11 in which said spools are molded with voids or flutes therein to vary compliance and final compressed shape.

13. A body mountable, springable frame adapted to be compressed between the chest and thighs of a worker, upon the worker bending down, so as to push upwards on the chest and assist the worker to stand up again, comprising:
    a belt worn around the waist of the worker;

spools of a flexible compressible material attached to the belt in line with the normal bending axis of the worker;

arcuate, flexible, torsion springs adapted to fit closely about and on the spools over a distance more than half way around, but not all the way around, the circumference of the spools;

a chest-contacting upper frame portion connected to one end of said arcuate springs; and at least one thigh-contacting lower frame portion connected to the other end of said arcuate spring.

14. The frame of claim 13 in which said frame is sized to fit the anthropometric geometry of the wearer.

15. The frame of claim 14, including several holes in the belt to allow the spools to mount in the correct hole to achieve alignment with the bending axis of different size workers.

* * * * *